(12) United States Patent
Ryan et al.

(10) Patent No.: US 12,311,147 B2
(45) Date of Patent: May 27, 2025

(54) DUAL CHAMBER SYRINGE ASSEMBLY

(71) Applicant: Becton, Dickinson and Company, Franklin Lakes, NJ (US)

(72) Inventors: Kevin M. Ryan, Whitehouse Station, NJ (US); Angela Huenerfauth, Morristown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 144 days.

(21) Appl. No.: 17/229,151

(22) Filed: Apr. 13, 2021

(65) Prior Publication Data

US 2021/0322677 A1    Oct. 21, 2021

Related U.S. Application Data

(60) Provisional application No. 63/011,352, filed on Apr. 17, 2020.

(51) Int. Cl.
*A61M 5/19* (2006.01)
*A61M 5/315* (2006.01)
(Continued)

(52) U.S. Cl.
CPC .......... *A61M 5/19* (2013.01); *A61M 5/31501* (2013.01); *A61M 5/31505* (2013.01);
(Continued)

(58) Field of Classification Search
CPC .. A61M 2005/1787; A61M 2005/3132; A61M 2005/31506; A61M 2005/31516; A61M 2005/31598; A61M 5/1407; A61M 5/1409; A61M 5/16804; A61M 5/16827; A61M 5/19; A61M 5/281; A61M 5/284; A61M 5/30; A61M 5/3134;
(Continued)

(56) References Cited

U.S. PATENT DOCUMENTS

| 4,529,403 A | * | 7/1985 | Kamstra | A61M 5/2066 604/191 |
| 4,792,329 A | * | 12/1988 | Schreuder | A61M 5/284 604/191 |

(Continued)

FOREIGN PATENT DOCUMENTS

| JP | S6214863 A | | 1/1987 | |
| JP | H09628 A | * | 1/1997 | ............ A61M 5/284 |
| JP | H09225029 A | | 9/1997 | |

OTHER PUBLICATIONS

PCT International Search Report and Written Opinion in PCT/US2021/027217 dated Jul. 27, 2021, 12 pages.

*Primary Examiner* — Shefali D Patel
(74) *Attorney, Agent, or Firm* — Servilla Whitney LLC (57) ABSTRACT

A syringe having two variable volumes are described herein. The syringe includes a first stopper and a second stopper, the first stopper being connected to a plunger. A first variable volume of the two variable volumes is disposed between the first stopper and the second stopper and a second variable volume of the two variable volumes is between the second stopper and a distal end of a barrel of the syringe. A flow path structure is disposed at the distal end of the barrel, the flow path structure extending from the distal end of the barrel along an inner sidewall of the barrel.

19 Claims, 10 Drawing Sheets

(51) Int. Cl.
  *A61M 5/168*  (2006.01)
  *A61M 5/178*  (2006.01)
  *A61M 5/31*   (2006.01)

(52) U.S. Cl.
  CPC .... *A61M 5/31511* (2013.01); *A61M 5/31515* (2013.01); *A61M 5/31596* (2013.01); *A61M 5/16827* (2013.01); *A61M 2005/1787* (2013.01); *A61M 2005/3132* (2013.01); *A61M 2005/31506* (2013.01)

(58) Field of Classification Search
  CPC .......... A61M 5/31501; A61M 5/31505; A61M 5/31511; A61M 5/31515; A61M 5/31596
  See application file for complete search history.

(56) References Cited

U.S. PATENT DOCUMENTS

2002/0035351 A1*  3/2002  Lodice .................. A61M 5/284
                                                        604/221
2008/0255521 A1  10/2008  Kubo et al.
2019/0038836 A1   2/2019  Lumkemann et al.

* cited by examiner

DUAL CHAMBER SYRINGE ASSEMBLY

CROSS-REFERENCE TO RELATED APPLICATIONS

This application claims priority to U.S. Provisional Application No. 63/011,352, filed Apr. 17, 2020, the entire disclosure of which is hereby incorporated by reference herein.

TECHNICAL FIELD

Aspects of the present disclosure relate to a dual chamber syringe assembly for administering two gases or fluids, or for administering and flushing catheters and other vascular accessing devices (VADs) and methods of flushing a catheter.

BACKGROUND

VADs are commonly used therapeutic devices and include IV catheters. There are two general classifications of VADs, peripheral catheters and central venous catheters. If not properly maintained, VADs can become occluded. To ensure VADs are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 ml to 20 ml.

For flush procedures, an I.V. line refers to a system containing a VAD, a tubing set with clamp and may terminate with a port or valve. The most common types of ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula in order to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain structure for delivering fluid from a storage compartment in the valve to the catheter, and are referred to in the art as positive displacement valves.

The removal of debris or residue is referred to as "purging" or "flushing" and prevents the build-up of deposits of blood, blood residue and IV drugs within a catheter or other VAD device. Such build-up can cause partial or complete blockage of the fluid pathway in a catheter system and can also require expensive and potentially dangerous methods for purging the affected catheter or a total catheter exchange. Often, such blockages lead to interruptions in therapy that may compromise patient care. The build-up of residue within a catheter can also increase infection risk by providing a breeding medium for microorganisms.

As is understood by one skilled in the art, flushing techniques involve injecting a flush solution, e.g., a saline solution, into VADs to clear debris and blockage. Injection is commonly done by a advancing a plunger rod into a pre-filled syringe barrel thereby expelling the flush solution into the VAD. When such techniques are used in conjunction with catheters, turbulence is introduced within the catheter, moving any debris or residue attached to the catheter. Flushing techniques require the application of substantially constant pressure or force to the plunger rod in the distal direction. Conventional or smooth flushing techniques may also include the application of pressure or force that increases or decreases substantially linearly to the plunger rod in the distal direction.

After flushing, the practitioner is then able to administer a dosage of medical fluid, the fluid being in a vial which requires withdraw or in a separate pre-filled syringe. However, the connecting of multiple devices to a VAD introduces the connectors to an unsterile outside environment, thereby introducing the possibility of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures.

Administration of intravenous medication followed by IV flush, typically utilize two separate syringes in clinical practice.

There is a need for a syringe assembly which has the means to both flush a VAD and administer a dosage of medical fluid, thereby reducing the risk of CRBSI. There is also a need for a single syringe for administration of intravenous medication followed by IV flush, to increase clinician efficiency and to reduce medical waste which conveys an environmental benefit.

SUMMARY

A first aspect of the present disclosure pertains to a flush syringe assembly comprising a substantially cylindrically shaped barrel, a plunger, a first and second stopper, a first and second variable volume and a flow path structure. The substantially cylindrically shaped barrel has an open proximal end, a proximal end and an inner sidewall, from a distal end extends a needleless connector and a lumen therethrough, the lumen being in fluid communication with a cavity of the barrel, the cavity being defined by the open proximal end, the distal end and the inner sidewall. The plunger is disposed within the barrel having plunger rod. The distal end includes a connection feature extending distally from the distal end. The first stopper is disposed proximal to the second stopper, the first stopper comprising a proximal end, a distal end and an outer surface the proximal end including an aperture configured to receive the connection feature of the plunger rod. The second stopper is disposed proximal to the distal end of the barrel, the second stopper comprising a proximal end, a distal end and an outer surface. The first variable volume is disposed between the first stopper and the second stopper. The second variable volume is between the second stopper and the distal end of the barrel. The flow path structure is disposed at the distal end of the barrel, the flow path structure extending from the distal end of the barrel along the inner sidewall of the barrel.

In one or more embodiments, the flow path structure is a protrusion extending from the inner sidewall of the barrel, the protrusion having a semicircular cross-sectional shape. In one or more embodiments, the flow path structure is a protrusion extending from the inner sidewall of the barrel, the protrusion having a convex cross-sectional shape.

In one or more embodiments, the flow path structure is a protrusion extending from the inner sidewall of the barrel, the protrusion having a concave cross-sectional shape. In one or more embodiments, the flow path structure is a unitary body molded into the inner sidewall of the barrel. In one or more embodiments, the flow path structure is a non-unitary body assembled into the inner sidewall of the barrel.

In one or more embodiments, the first stopper further comprises a plurality of radial ribs disposed on the outer surface of the first stopper.

In one or more embodiments, the second stopper further comprises a plurality of radial ribs disposed on the outer surface of the second stopper.

In one or more embodiments, the proximal end of the second stopper has an inwardly conical shape configured to receive a distal end of the first stopper.

In one or more embodiments, the distal end of the second stopper has an outwardly conical shape configured to conform and to be received by the distal end of the barrel.

In one or more embodiments, the connection feature comprises a plurality of threads for engaging a plurality of female threads integral to the aperture of the first stopper.

In one or more embodiments, the needleless connector is integral with the distal end of the barrel.

In one or more embodiments, the flow path structure extends at least the length of the second stopper, thereby creating a flow path between the second stopper and the inner sidewall of the barrel when the second stopper abuts the distal end of the barrel.

In one or more embodiments, when the second stopper fully abuts the distal end of the barrel, the flow path structure creates a flow path from the second variable volume to the lumen of the needleless connector.

In one or more embodiments, advancement of the second stopper against the distal end of the barrel causes deformation of the second stopper due to the flow path structure interfering with the second stopper.

In one or more embodiments, advancement of the second stopper against the distal end of the barrel causes a flow path between the second stopper and the syringe barrel.

In one or more embodiments, the distal end of the barrel has a frustoconical shape.

In one or more embodiments the flow path structure follows the frustoconical shape of the distal end of the barrel. In one or more embodiments the flow path structure extends to the lumen of the needleless connector.

In one or more embodiments, the flow path structure has a sloped proximal end, thereby allowing less restrictive advancement of the second stopper against the flow path structure.

In one or more embodiments, the flow path structure has a first thickness profile TP1 along the inner sidewall of the barrel and a second thickness profile TP2 along the distal end of the barrel. In one or more embodiments, the first thickness profile TP1 is greater than the second thickness profile TP2.

In one or more embodiments, the syringe being in an initial state, an intermediate state and a final state. In one or more embodiments, the initial state is defined by the plunger being in a fully retracted position in the cavity, and the first stopper and second stopper are separated within the cavity by the first variable volume, and the second stopper and distal end of the barrel are separated within the cavity by the second variable volume. In one or more embodiments, the intermediate state is defined by the plunger being in a partially advanced position in the cavity, and the second stopper has been fully advanced against the distal end of the barrel, the advancement of the second stopper causing expulsion of contents of the second variable volume through the lumen, thereby essentially eliminating the second variable volume. In one or more embodiments, the final state is defined by the plunger being in a fully advanced in the cavity, and the distal end of the first stopper abuts the proximal end of the second stopper, thereby eliminating the first variable volume.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

In this disclosure, a convention is followed wherein the distal end of the device is the end closest to a patient and the proximal end of the device is the end away from the patient and closest to a practitioner.

With respect to terms used in this disclosure, the following definitions are provided. As used herein, the use of "a," "an," and "the" includes the singular and plural. As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD) Luer connector also has a distal end channel that releasably attaches the Luer connector to the hub of a VAD, and a proximal end channel that releasably attaches the Luer connector to the barrel of a syringe.

As used herein, ISO 80369-7:2016 defines a specification for standard Luer connectors including a 6% taper between the distal end and the proximal end. A male standard luer connector increases from the open distal end to the proximal end. A female standard luer connector decreases from the open proximal end to the distal end. According to ISO 80369-7:2016, a male standard luer connector has an outer cross-sectional diameter measured 0.75 mm from the distal end of the tip of between 3.970 mm and 4.072 mm. The length of the male standard luer taper is between 7.500 mm to 10.500 mm. The outer cross-sectional diameter measured 7.500 mm from the distal end of the tip is between 4.376 mm and 4.476 mm. As used herein, the phrases "male standard luer connector" and "female standard luer connector" shall refer to connectors having the dimensions described in ISO 80369-7, which is hereby incorporated by reference in its entirety.

As would be readily appreciated by skilled artisans in the relevant art, while descriptive terms such as "tip", "hub", "thread", "protrusion/insert", "tab", "slope", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In an exemplary implementation of the embodiments of present disclosure, a barrel of a syringe includes a distal end having a needleless connection. In one or more embodiments, the needleless connection includes at least one thread and other features in any and all combinations allowing it to interface with a corresponding thread or plurality of threads of a corresponding connector.

According to further exemplary implementations of the embodiments of the present disclosure, configuration of structural elements making up the needleless connector include a collar protruding from the distal end of the barrel, the collar comprising at least one thread to connect to the corresponding thread or plurality of threads of a corresponding connector.

According to still further exemplary implementations of the embodiments of the present disclosure, the collar or the needleless connector generally may bend or elastically deform in order to allow better interference fit compliance with corresponding connectors.

According to still further exemplary implementations of the embodiments of the present disclosure, the needleless connector may comprise female threads that are sized and have a thread pattern that will engage with a standard ISO594-2 type of male fitting and/or a male threads that are sized and have a thread pattern that will engage with a standard ISO594-2 type of female fitting. An example of an ISO594-2 type of fitting is a Q-style fitting.

In one or more embodiments, a female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end or a stopcock.

Referring now to the drawings, wherein like reference numerals designate identical or corresponding parts throughout the several views, embodiments of the present disclosure are described as follows.

Figure 1:
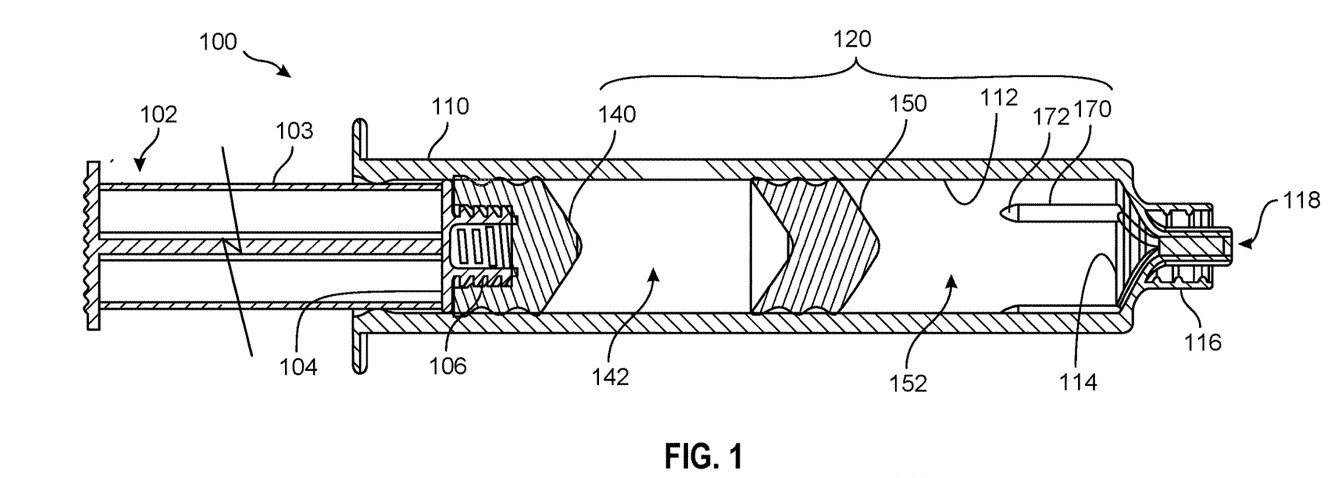
FIG. 1 show a cross-sectional view of a syringe assembly in an initial state.
Figure 2:
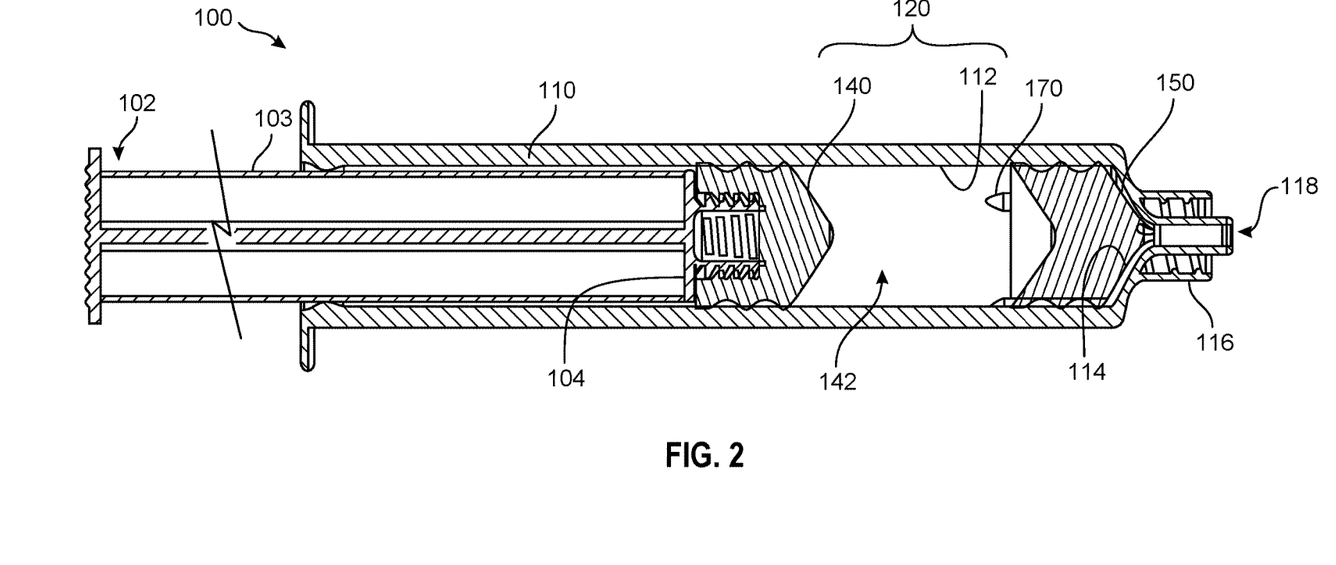
FIG. 2 shows cross-sectional view of the syringe assembly of FIG. 1 in an intermediate state.

A first aspect of the present disclosure relates to a syringe 100 having a barrel 110 and a plunger 102. As shown in FIGS. 1 and 2, the barrel 110 is of a cylindrical shape having an open proximal end, a distal end 114 and an inner sidewall 112. From the distal end 114 extends a needleless connector 116, the needleless connector 116 being integral with the distal end 114. The needleless connection 116 has a lumen 118 extending therethrough, the lumen 118 being in fluid communication with a cavity 120 of the barrel 110, the cavity 120 being defined by the open proximal end, distal end 114 and inner sidewall 112 of the barrel 110. The distal end 114 has a frustoconical shape.

The plunger 102 comprises a plunger rod 103 having a distal end 104 connected to a first stopper 140. The distal end 104 of the plunger rod 103 includes a connection feature 106 extending distally from the distal end 104 of the plunger rod 103. The connection feature 106 is configured to removably or non-removably connect to the first stopper 140. In one or more embodiments, the connection feature 106 connects to a first stopper 140 by way of a threaded connection. In one or more embodiments, the connection feature 106 connects to first stopper 140 by way of an interference fit. In one or more embodiments, the connection feature 106 connects to first stopper 140 by way of a snap-fit. In one or more embodiments, the connection feature 106 connects to first stopper 140 by way of a twist-lock fit. In one or more embodiments, the connection feature 106 connects to first stopper 140 by way of sonic welding or a medical grade adhesive. In one or more embodiments, first stopper 140 is integrally formed to the distal end 104 of the plunger rod 103.

As shown in FIGS. 1 and 2, disposed within the cavity 120 are at least two stoppers, the at least two stoppers including a first stopper 140 and a second stopper 150. The second stopper 150 is disposed proximal to the distal end 114 of the barrel 110, and the first stopper 140 is disposed proximal to the second stopper 150. Between the second stopper 150 and the distal end 114 is a first variable volume 142, the first variable volume 142 being within the cavity 120. Between the first stopper 140 and second stopper 150 and is a second variable volume 152, the second variable volume 152 being within the cavity 120.

Figure 3A:
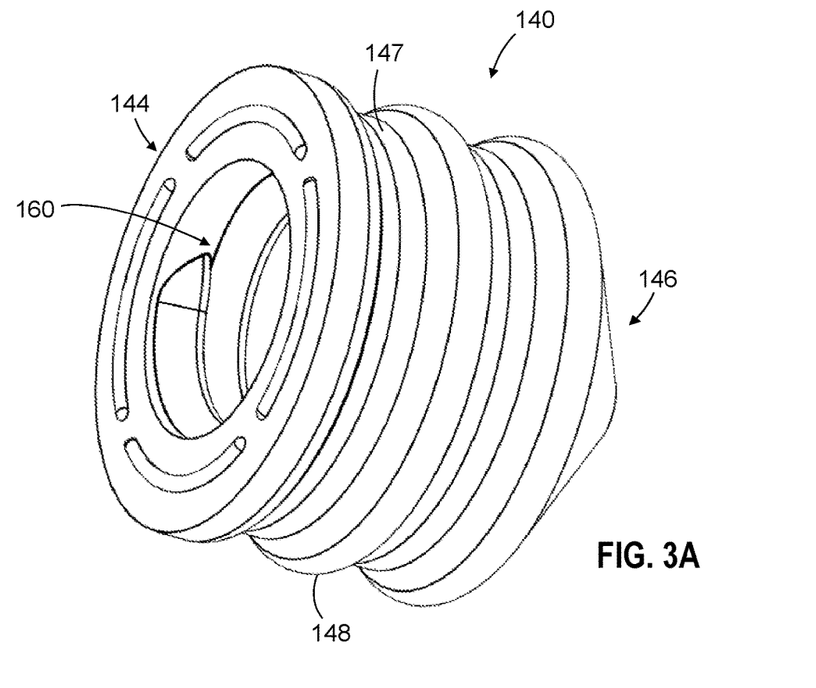
FIGS. 3A and 3B illustrate perspective views of a first stopper of the syringe assembly of FIG. 1.
Figure 3B:
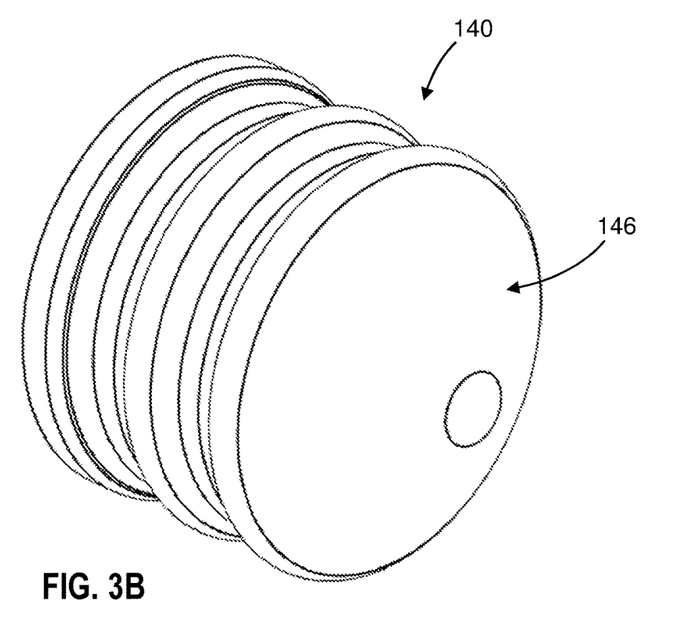
Figure 3C:
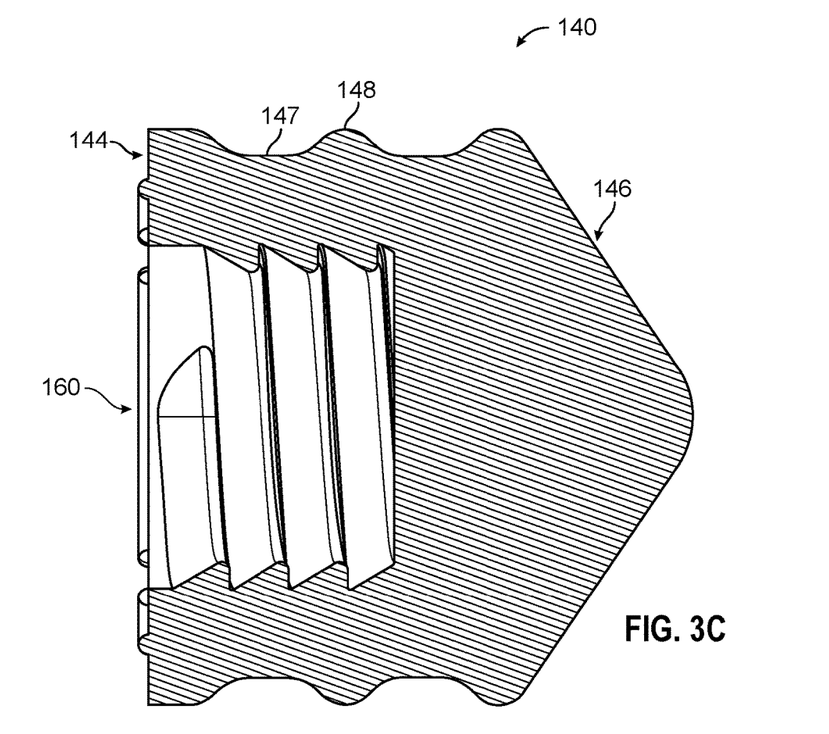
FIG. 3C illustrates a cross-sectional view of the first stopper of FIG. 3A.

As shown in FIGS. 3A-3C, the first stopper 140 comprises a proximal end 144, a distal end 146 and an outer surface 147 disposed between the proximal end 144 and the distal end 146. In one or more embodiments, the proximal end 144 includes an aperture 160 for receiving the connection feature 106 of the plunger rod 103. In one or more embodiments, the aperture 160 includes a plurality of female threads for engaging the connection feature 106 of the plunger rod 103. In one or more embodiments, the proximal end 144 further includes a plurality of radial protrusions. The distal end 146 of the first stopper 140 has an outwardly conical shape. In one or more embodiments, the distal end 146 has a frustoconical shape. In one or more embodiments, the outer surface 147 of the first stopper 140 includes a plurality of radial ribs 148.

Figure 4A:
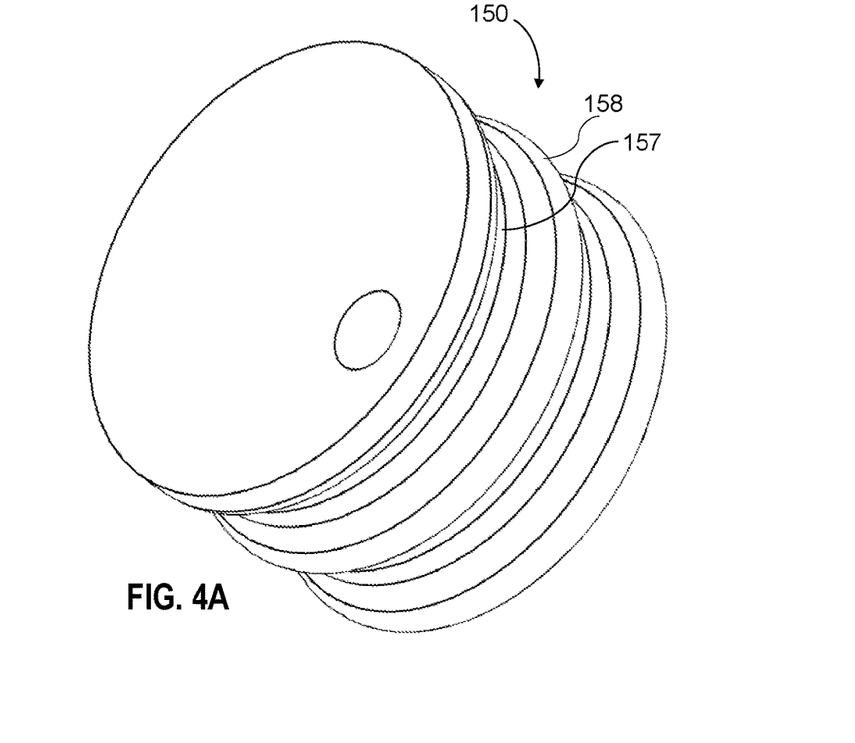
FIGS. 4A and 4B illustrate perspective views of a second stopper of the syringe assembly of FIG. 1.
Figure 4B:
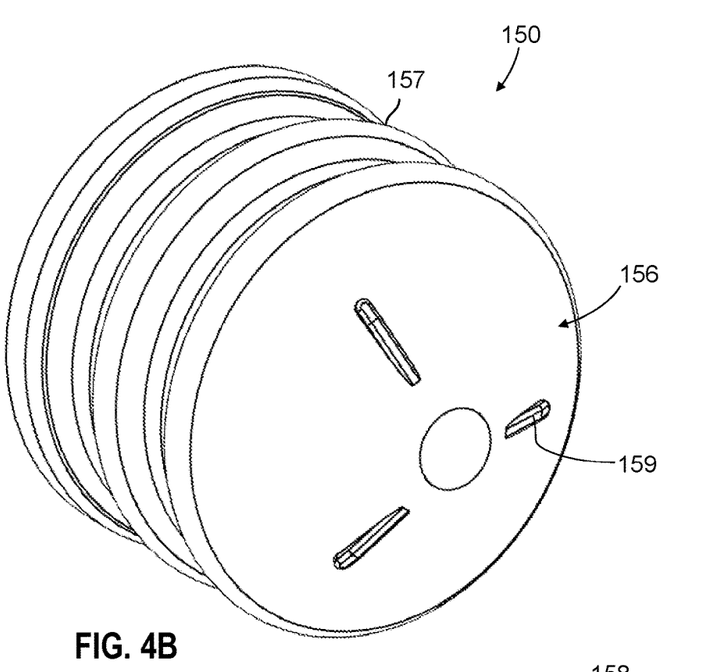
Figure 4C:
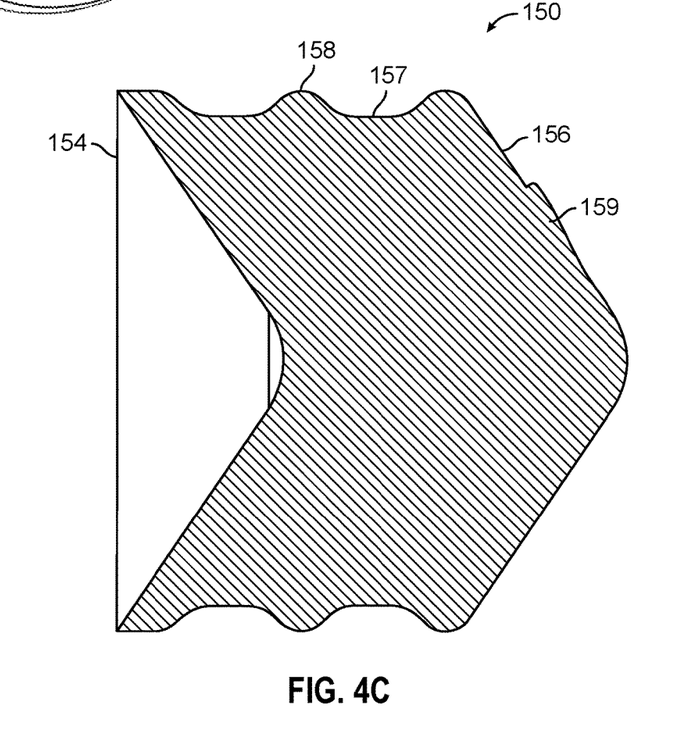
FIG. 4C illustrates a cross-sectional view of the second stopper of FIG. 4A.

As shown in FIGS. 4A-4C, the second stopper 150 comprises a proximal end 154, a distal end 156 and an outer surface 157 disposed between the proximal end 154 and the distal end 156. The proximal end 154 of the second stopper 150 has an inwardly conical shape configured receive a distal end (not shown) of the first stopper 140. The distal end 156 of the second stopper 150 has an outwardly conical shape. The outwardly conical shape of the distal end 156 of the second stopper 150 is configured to conform to and be received by the distal end 114 of the barrel 110. In one or more embodiments, the outer surface 157 of the second stopper 150 includes a plurality of radial ribs 158. In one or more embodiments, the distal end 156 includes a plurality of axial ribs 159, the axial ribs 159 facing towards the center of the second stopper 150. In one or more embodiments, the proximal end 154 has a frustoconical shape. In one or more embodiments, the distal end 156 has a frustoconical shape.

Referring back to FIG. 1, the first stopper 140 is connected to a distal end 104 of a plunger rod 103 by means of the connection feature 106, the plunger being advanced within the cavity 120 of the barrel 110. In the preferred embodiment, the connection feature 106 is at least one male thread disposed on the distal end 104 of the plunger rod 103, the at least one male thread connected to a female thread disposed within the aperture 160 of the first stopper 140.

Figure 5A:
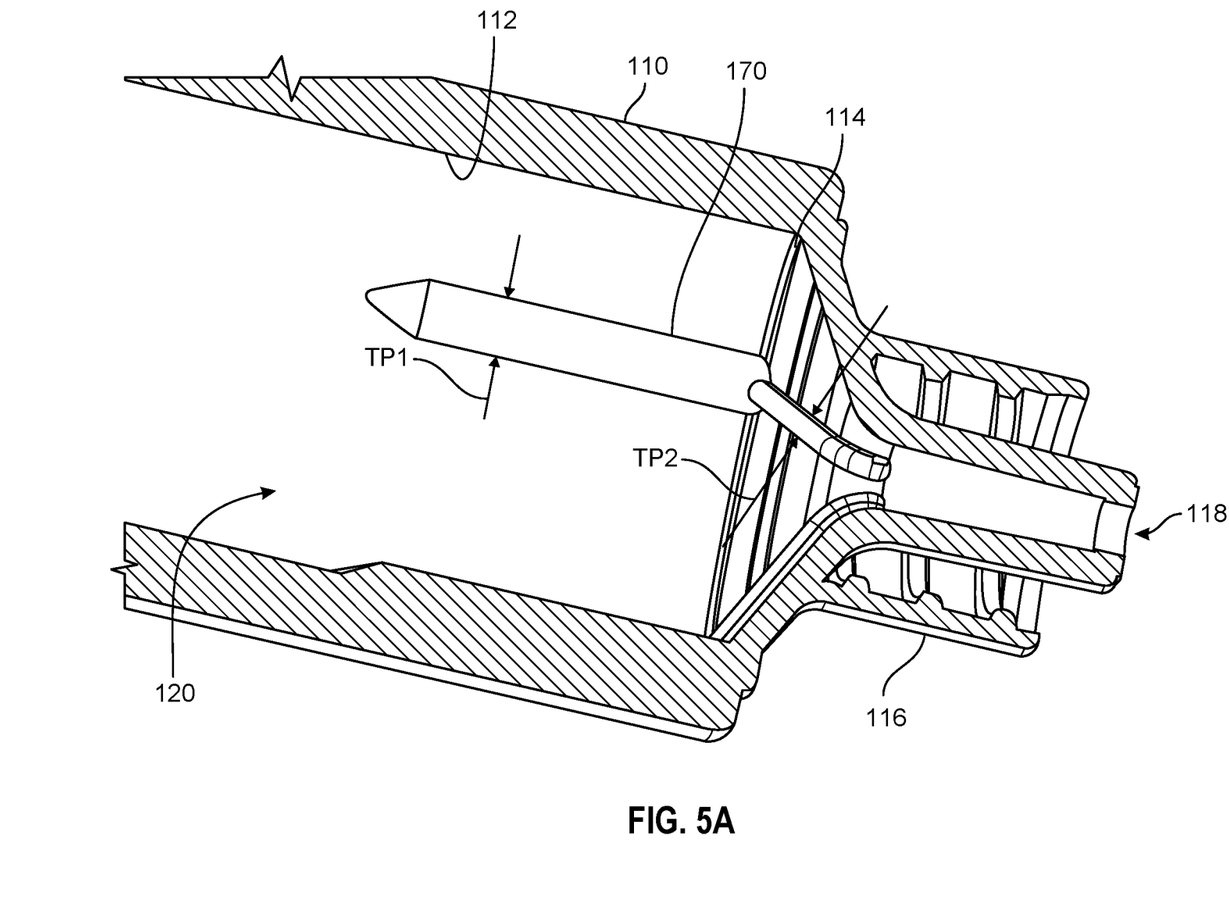
FIGS. 5A through 5D illustrate cross-sectional views of the syringe assembly of FIG. 1 in a final state; and, FIGS. 6A and 6B illustrate cross-sectional view of the syringe assembly of FIG. 1 in the final state.
Figure 5B:
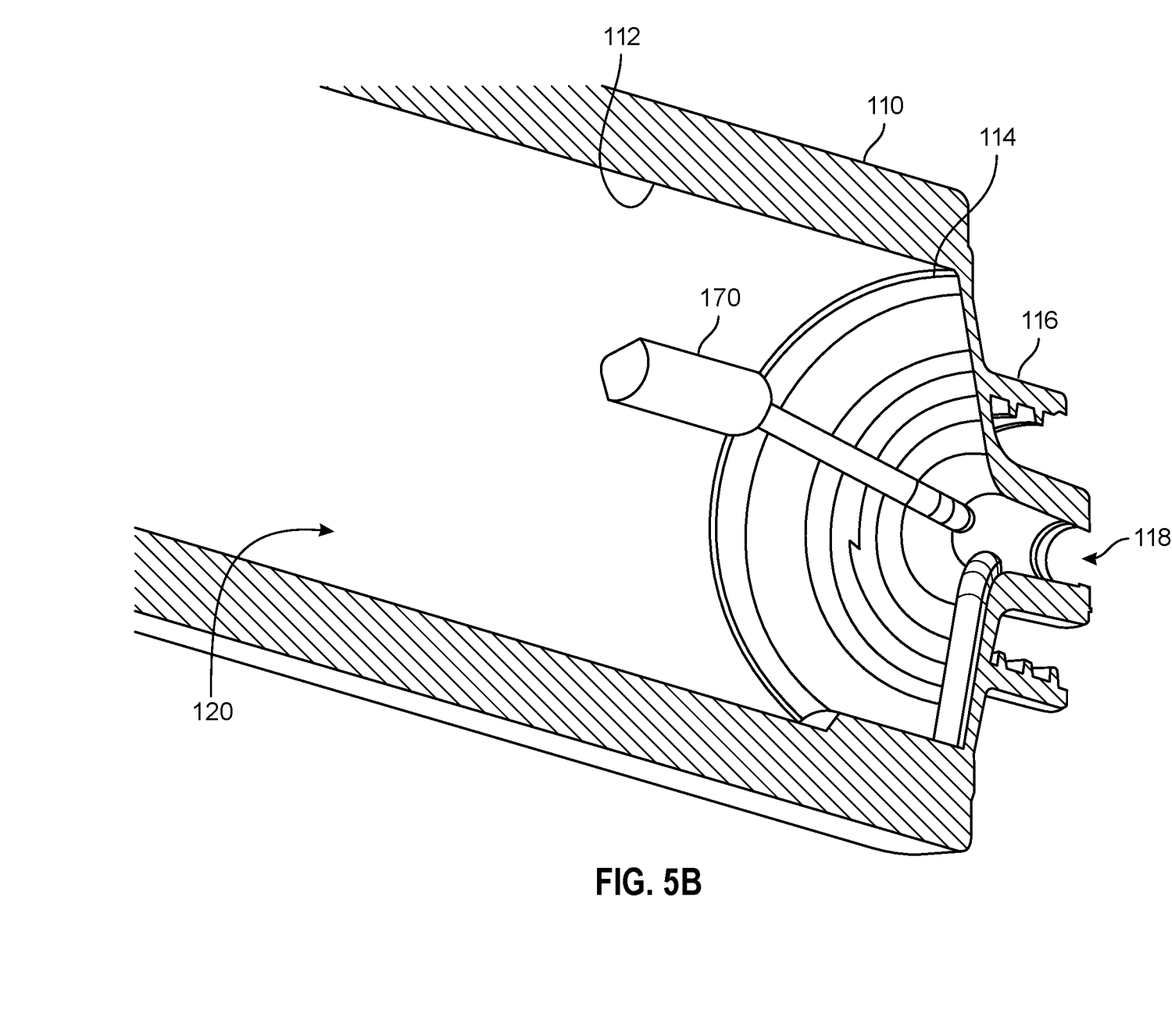
Figure 5C:
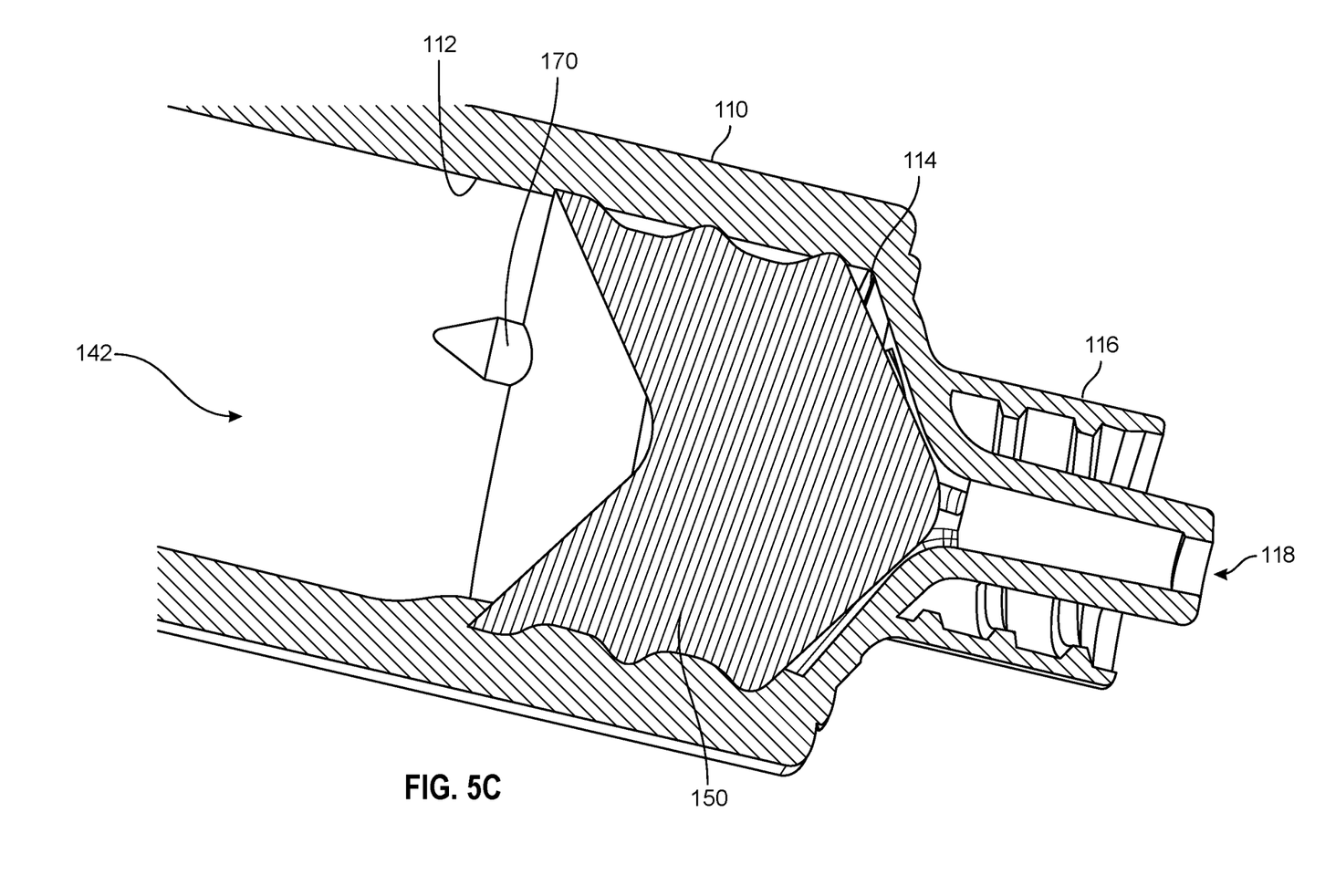
Figure 5D:
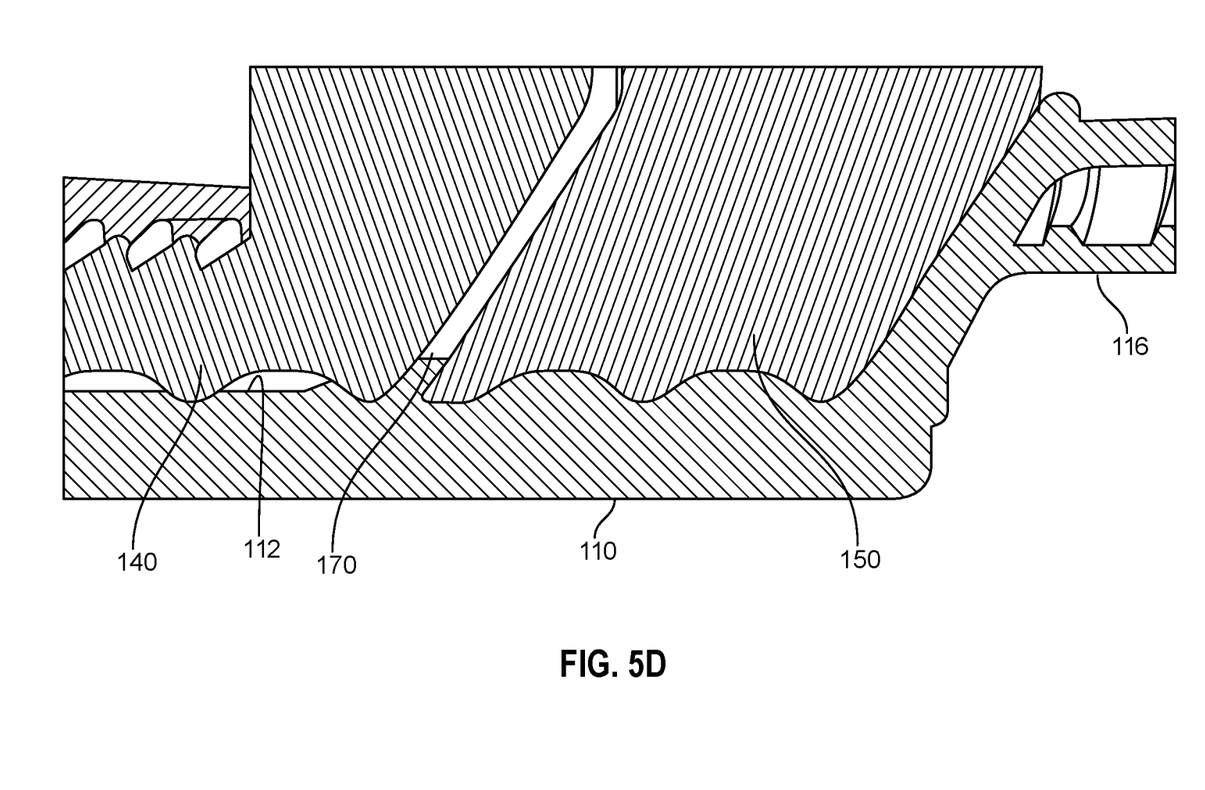

A second aspect of the present disclosure relates to a flow path structure 170 disposed at the distal end 114 of the barrel 110. As shown in FIGS. 5A-5D, the flow path structure extends from the distal end 114 along the inner sidewall 112 of the barrel 110. As shown in FIGS. 5C and 5D, advancement of the second stopper 150 against the distal end 114 of the barrel 110 causes deformation of the second stopper 150 due to the flow path structure 170 interfering with the second stopper 150.

The deformation of the second stopper 150 allows for flow of fluid between the flow path structure 170 and the second stopper 150. In particular, as best shown in FIG. 5C, the flow path structure 170 extends at least the length of the second stopper 150, thereby creating a flow path between the second stopper 150 and the inner sidewall 112 of the barrel 110 when the second stopper 150 abuts the distal end 114 of the barrel 110. As shown in FIGS. 5A and 5B, the flow path structure 170 follows the frustoconical shape of the distal end 114 of the barrel 110. In one or more embodiments, the flow path structure 170 extends to the lumen 118 of the needleless connector 116. As shown in FIG. 5C, when the second stopper 150 fully abuts the distal end 114 of the barrel 110, the flow path structure 170 creates a flow path from the second variable volume 152 to the lumen 118 of the needleless connector 116. In one or more embodiments the flow path structure 170 has a sloped proximal end 172, thereby allowing less restrictive advancement of the second stopper 150 against the flow path structure 170. In one or more embodiments, as best shown in FIG. 5B, the flow path structure 170 has a first thickness profile TP1 along the inner sidewall 112 of the barrel 110 and a second thickness profile TP2 along the frustoconical shape of the distal end 114 of the barrel 110. In one or more embodiments, the first thickness profile TP1 is greater than the second thickness profile TP2.

In one or more embodiments, the flow path structure 170 is in the form of a protrusion extending from the inner sidewall 112 of the barrel 110, the protrusion having a semicircular or convex cross-sectional shape. In one or more embodiments, the flow path structure 170 is in the form of a protrusion extending from the inner sidewall 112 of the barrel 110, the protrusion having a concave cross-sectional shape.

In one or more embodiments, wherein the flow path structure 170 is a unitary body molded into the inner sidewall 112 of the barrel 110. In one or more embodiments, the flow path structure 170 is a non-unitary body assembled into the inner sidewall 112 of the barrel 110.

Figure 6A:
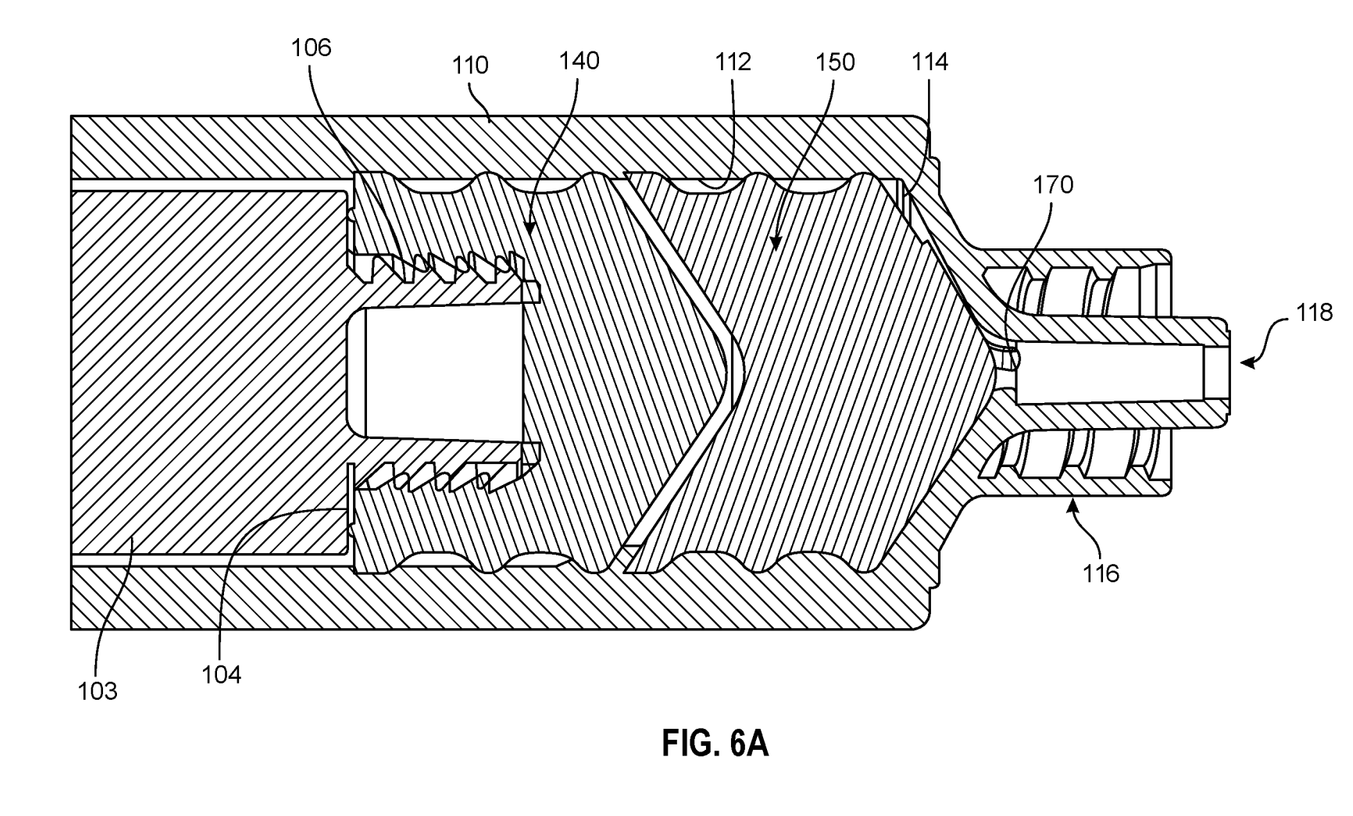
Figure 6B:
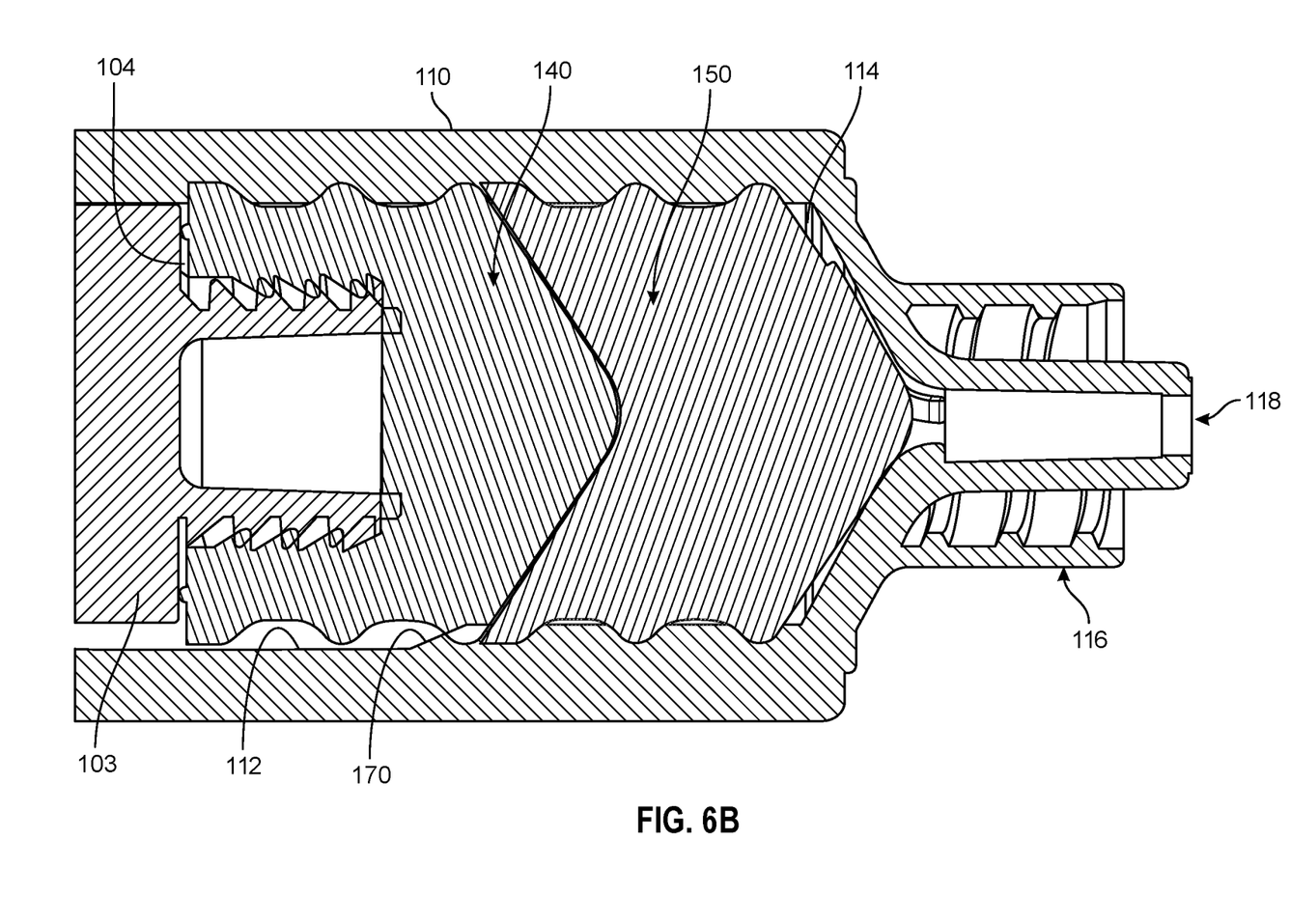

FIG. 1 illustrates the syringe 100 in an initial state, wherein the first stopper 140 and second stopper 150 are separated within the cavity 120 by the first variable volume 142 and the second variable volume 152. In the initial state the plunger is in a further retractable position. FIG. 2 illustrates the syringe 100 in an intermediate state wherein the plunger 102 has been partially advanced into the cavity 120. In the intermediate state, the second stopper 150 has been fully advanced against the distal end 114 of the barrel 110, the advancement causing the expulsion of the contents of the second variable volume 152 through the lumen 118, thereby essentially eliminating the second variable volume 152. FIGS. 6A and 6B illustrate the syringe 100 in a final state wherein the plunger 102 has been fully advanced into the cavity 120, wherein the distal end 146 of the second stopper 150 abuts the distal end 114 of the barrel 110, thereby essentially eliminating the second variable volume 152. For purposes of illustration as shown in FIG. 6A, a space is depicted between the first stopper 140 and second stopper 150 in the final state, however, as shown in FIG. 6B, the first stopper 140 fully abuts the second stopper 150 in the final state.

As the first stopper 140 is advanced in a distal direction within the cavity 120 by way of advancing the plunger 102, due to fluid being incompressible, an increase in fluid pressure to the first variable volume 142 causes the second stopper 150 to move in a distal direction causing the fluid or contents of the second variable volume 152 to eject from the lumen 118 of the needleless connector 116. Upon advancement of the first stopper 140 in a distal direction to the final state the further increase in fluid pressure causes the fluid or contents of the first variable volume 142 to eject through the flow path created by the flow path structure 170 through the lumen 118 of the needleless connector 116. Laminar flow can be provided in a relatively controlled manner by steadily advancing the plunger 102 into the barrel 110.

In one or more embodiments, the first variable volume 142 is filled with a desired amount of a saline flush fluid. In one or more embodiments, the first variable volume 142 is filled with a desired medicine. In one or more embodiments, the second variable volume 152 is filled with a desired amount of a saline flush fluid. In one or more embodiments, the second variable volume 152 is filled with a desired medicine. In one or more embodiments, the first variable volume 142 and the second variable volume 152 is filled with desired amounts of saline flush fluid. In one or more embodiments, the first variable volume 142 and the second variable volume 152 is filled with desired amounts of medicine. In addition, the barrel 110 of the syringe 100 may include measuring indicia to indicate the amount of flush solution contained within. The first variable volume 142 and the second variable volume 152 may be pre-filled with flush solution during or after the assembly of the syringe 100 using sterile filling methods.

Exemplary flush solutions include saline flush solution and/or heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml.

The syringe 100 described herein may also include visual or other indication elements to indicate the position of the first stopper 140 and the second stopper 150.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A syringe comprising:
a substantially cylindrically shaped barrel having an open proximal end, a frustoconical shaped distal end, and an inner sidewall, the distal end of the barrel having a needleless connector, a lumen extending through the needleless connector, the lumen being in fluid communication with a cavity of the barrel, the cavity being defined by the open proximal end, the distal end and the inner sidewall;
a plunger disposed within the barrel having a plunger rod and a distal end, the distal end of the plunger including a connection feature extending distally from the distal end of the plunger;
a first stopper disposed proximal to a second stopper, the first stopper comprising a proximal end, a distal end and an outer surface, the first stopper further comprising a first plurality of radial ribs disposed on the outer surface of the first stopper, the proximal end of the first stopper including an aperture configured to receive the connection feature of the distal end of the plunger;
the second stopper disposed proximal to the distal end of the barrel, the second stopper comprising a proximal end, a distal end and an outer surface, the second stopper further comprising a second plurality of radial ribs disposed on the outer surface of the second stopper;
a first variable volume, the first variable volume being disposed between the first stopper and the second stopper;
a second variable volume, the second variable volume being between the second stopper and the distal end of the barrel; and
a flow path structure disposed at the distal end of the barrel, the flow path structure extending from the lumen of the needleless connector along the inner sidewall of the barrel, the flow path structure having a first uniform cross-sectional thickness profile extending proximally away from the frustoconical shaped distal end along the inner sidewall of the barrel and a second uniform cross-sectional thickness profile extending along an entire length of the frustoconical shaped distal end, wherein the first uniform cross-sectional thickness profile of the flow path structure is greater than the second uniform cross-sectional thickness profile of the flow path structure, the flow path structure is a protrusion extending from the inner sidewall of the barrel to cause deformation of the second stopper, and the flow path structure extends at least a length of the second stopper, thereby creating a flow path between the second stopper and the inner sidewall of the barrel and creating a flow path from the first variable volume to the lumen of the needleless connector when the second stopper abuts the distal end of the barrel.

2. The syringe of claim 1, the protrusion having a semi-circular cross-sectional shape.

3. The syringe of claim 1, the protrusion having a convex cross-sectional shape.

4. The syringe of claim 1, the protrusion having a concave cross-sectional shape.

5. The syringe of claim 1, wherein the flow path structure is a unitary body molded into the inner sidewall of the barrel.

6. The syringe of claim 1, wherein the flow path structure is a non-unitary body assembled into the inner sidewall of the barrel.

7. The syringe of claim 1, wherein the proximal end of the second stopper has an inwardly conical shape configured to receive the distal end of the first stopper.

8. The syringe of claim 1, wherein the distal end of the second stopper has an outwardly conical shape configured to conform and to be received by the distal end of the barrel.

9. The syringe of claim 1, wherein the connection feature comprises a plurality of threads for engaging a plurality of female threads integral to the aperture of the first stopper.

10. The syringe of claim 1, wherein the needleless connector is integral with the distal end of the barrel.

11. The syringe of claim 1, wherein advancement of the second stopper against the distal end of the barrel causes the deformation of the second stopper due to the flow path structure interfering with the second stopper.

12. The syringe of claim 11, wherein the advancement of the second stopper against the distal end of the barrel causes the flow path between the second stopper and the inner sidewall of the barrel.

13. The syringe of claim 1, wherein the flow path structure has a sloped proximal end, thereby allowing less restrictive advancement of the second stopper against the flow path structure.

14. The syringe of claim 1, the syringe being in an initial state, an intermediate state and a final state.

15. The syringe of claim 14, wherein the initial state is defined by the plunger being in a fully retracted position in the cavity, and the first stopper and the second stopper are separated within the cavity by the first variable volume, and the second stopper and the distal end of the barrel are separated within the cavity by the second variable volume.

16. The syringe of claim 14, wherein the intermediate state is defined by the plunger being in a partially advanced position in the cavity, and the second stopper has been fully advanced against the distal end of the barrel, the advancement of the second stopper causing expulsion of contents of the second variable volume through the lumen, thereby essentially eliminating the second variable volume.

17. The syringe of claim 14, wherein the final state is defined by the plunger being in a fully advanced position in the cavity, and the distal end of the first stopper abuts the proximal end of the second stopper, thereby eliminating the first variable volume.

18. The syringe of claim 1, wherein the second stopper has a plurality of axial ribs disposed on the distal end of the second stopper.

19. The syringe of claim 1, wherein the flow path structure extends into the lumen of the needleless connector.

* * * * *